United States Patent [19]

Sofranko et al.

[11] Patent Number: 4,777,313

[45] Date of Patent: Oct. 11, 1988

[54] BORON-PROMOTED REDUCIBLE METAL OXIDES AND METHODS OF THEIR USE

[75] Inventors: John A. Sofranko, Malvern; Robert G. Gastinger, Brookhaven; C. Andrew Jones, Newtown Square, all of Pa.

[73] Assignee: Atlantic Richfield Company, Los Angeles, Calif.

[21] Appl. No.: 877,574

[22] Filed: Jun. 23, 1986

Related U.S. Application Data

[63] Continuation-in-part of Ser. No. 683,296, Dec. 18, 1984, abandoned, which is a continuation-in-part of Ser. No. 522,937, Aug. 12, 1983, Pat. No. 4,499,322, which is a continuation-in-part of Ser. No. 522,936, Aug. 12, 1983, Pat. No. 4,495,374, which is a continuation-in-part of Ser. No. 600,654, Apr. 16, 1984, Pat. No. 4,547,611, which is a continuation-in-part of Ser. No. 600,655, Apr. 16, 1984, abandoned.

[51] Int. Cl.$^4$ .................................................. C07C 2/00
[52] U.S. Cl. ............................ 585/500; 585/654; 585/656; 585/658; 585/661; 585/943
[58] Field of Search ............... 585/654, 656, 658, 661, 585/500, 943

[56] References Cited

U.S. PATENT DOCUMENTS

| | | | |
|---|---|---|---|
| 3,607,966 | 9/1971 | Croce | 585/658 |
| 3,670,042 | 6/1972 | Croce et al. | 585/658 |
| 3,810,953 | 5/1974 | Cichowski | 585/658 |
| 3,887,631 | 6/1975 | Yaffe | 585/658 |
| 3,927,138 | 12/1985 | Walker | 585/658 |
| 4,430,313 | 5/1984 | Eastman et al. | 585/661 |
| 4,495,374 | 1/1985 | Jones et al. | 585/500 |
| 4,499,322 | 2/1983 | Jones et al. | 585/500 |
| 4,507,517 | 3/1985 | De Vries et al. | 585/943 |
| 4,523,049 | 6/1985 | Jones et al. | 585/658 |
| 4,547,611 | 10/1986 | Jones et al. | 585/500 |
| 4,554,395 | 11/1985 | Jones et al. | 585/658 |

*Primary Examiner*—William R. Dixon, Jr.
*Assistant Examiner*—James M. Hunter, Jr.
*Attorney, Agent, or Firm*—Craig E. Larson

[57] ABSTRACT

Compositions comprising boron-promoted reducible metal oxides (especially reducible oxides of Mn) and optionally containing alkali and alkaline earth metal components are disclosed, as well as use thereof for hydrocarbon conversions characterized by formation of byproduct water. Particular processes comprise the conversion of methane to higher hydrocarbons and the dehydrogenation of dehydrogenatable hydrocarbons, e.g., dehydrogenation of $C_2$-$C_5$ alkanes to form the corresponding olefins.

41 Claims, No Drawings

BORON-PROMOTED REDUCIBLE METAL OXIDES AND METHODS OF THEIR USE

CROSS-REFERENCE TO RELATED APPLICATIONS

This application is a continuation-in-part of application Ser. No. 683,296 filed Dec.18, 1984, now abandoned, which in turn is a continuation-in-part of applications Ser. No. 522,937 filed Aug. 12, 1983, now U.S. Pat. No. 4,499,322, which is a continuation-in-part of application Ser. No. 522,936, filed Aug.12, 1983, now U.S. Pat. No. 4,495,374, which is a continuation-in-part of application Ser. No. 600,654 filed Apr. 16, 1984, now U.S. Pat. No. 4,547,611, which is a continuation-in-part of application Ser. No. 600,655 filed Apr. 16 1984, now abandoned.

BACKGROUND OF THE INVENTION

This invention relates to hydrocarbon conversion processes employing reducible metal oxide compositions. One particular application of this invention is a method for converting methane to higher hydrocarbons. Another particular application of this invention is a process for the oxidative dehydrogenation of hydrocarbons, especially a process for the oxidative dehydrogenation of paraffinic hydrocarbons to the corresponding mono-olefins.

A central aspect of the presently claimed invention is the catalyst composition employed in such hydrocarbon conversion processes. In one particular aspect, the present invention relates to compositions comprising alkaline earth promoted reducible metal oxides (especially reducible oxides of manganese). In one still more specific embodiment, this invention relates to compositions comprising oxides of Mn, alkaline earth metals, alkali metals and boron.

Recently, it has been discovered that methane may be converted to higher hydrocarbons by a process which comprises contacting methane and an oxidative synthesizing agent at synthesizing conditions (e.g., at a temperature selected within the range from about 500° to about 1000° C.). Oxidative synthesizing agents are compositions having as a principal component at least one oxide of at least one metal which compositions produce $C_2+$ hydrocarbon products, co-product water, and a composition comprising a reduced metal oxide when contacted with methane at synthesizing conditions. Reducible oxides of several metals have been identified which are capable of converting methane to higher hydrocarbons. In particular, oxides of manganese, tin, indium, germanium, lead, antimony, bismuth, praseodymium, terbium, cerium, iron and ruthenium are most useful. See commonly-assigned U.S. Pat. Nos.4,443,649 (Mn); 4,444,984 (Sn); 4,445,648 (In); 4,443,645 (Ge); 4,443,674 (Pb); 4,443,646 (Bi); 4,499,323 (Pr); 4,499,324 (Ce); and 4,593,139 (Ru), the entire contents of which are incorporated herein by reference. See also commonly-assigned U.S. patent application Ser. No. 06/666,694 (Fe) the entire content of which is incorporated herein by reference.

Commonly-assigned U.S. Pat. No.4,554,395 discloses and claims a process which comprises contacting methane with an oxidative synthesizing agent under elevated pressure (2-100 atmospheres) to produce greater amounts of $C_3+$ hydrocarbon products.

Commonly-assigned U.S. Pat. No.4,560,821 discloses and claims a process for the conversion of methane to higher hydrocarbons which comprises contacting methane with particles comprising an oxidative synthesizing agent which particles recirculate between two physically separate zones—a methane contact zone and an oxygen contact zone.

As noted, the reaction products of such processes are mainly ethylene, ethane, other light hydrocarbons, carbon oxides, coke and water. It would be beneficial to these oxidative synthesis processes to reduce selectivities to carbon oxides and coke.

Hydrocarbon conversion processes employing the composition of this invention are characterized by relatively severe reaction conditions and by the formation of coproduct water. Thus, hydrothermal stability at elevated temperatures (e.g., 500° to 1000° C.) is an important criterion for the compositions. Moreover, uses contemplated for the present compositions require catalysts which are rugged, attrition-resistant, and stable at high temperatures. It is also desirable that the compositions are able to operate effectively for relatively long periods while cycling between oxidized and reduced states.

An object of the present invention is a composition and process for hydrocarbon conversion processes, especially for processes characterized by the formation of byproduct water. A related object is a rugged, stable, attrition-resistant oxidant composition for such processes.

Another object of the present invention is a composition and process for converting methane to higher hydrocarbons, especially for processes characterized by the formation of byproduct water. A related object is a rugged, stable, attrition-resistant oxidant composition for such methane conversion process.

Still another object of the present invention is a composition and process for the oxidative dehydrogenation of hydrocarbons. A related object is a rugged, stable, attrition-resistant oxidant composition for such processes. Another related object is a composition and process for the oxidative dehydrogenation of paraffinic hydrocarbons to form the corresponding mono-olefins.

Other objects, aspects and advantages of the invention will be apparent to those skilled in the art upon studying the specification and the appended claims.

SUMMARY OF THE INVENTION

It has now been found that hydrocarbon conversions (especially the conversion of methane to higher hydrocarbons) wherein a hydrocarbon feed is contacted at elevated temperatures with a solid comprising a reducible metal oxide is improved when the contacting is conducted in the presence of a promoting amount of at least one member of the group consisting of boron and compounds thereof. Examples of reducible metal oxides are oxides of Mn, Sn, In Ge, Pb, Sb, Bi, Pr, Tb, Ce, Fe and Ru. However, distinct embodiments of the present invention are directed toward processes and catalyst compositions comprising reducible oxides of Mn. In certain embodiments of this invention, the catalyst compositions are characterized by the substantial absence of catalytically effective iron, to distinguish known oxidative dehydrogenation catalysts based on the use of Mn ferrites.

One class of catalyst compositions useful in the process of this invention comprises:
 (1) at least one reducible metal oxide, (2) at least one member of the group consisting of boron and compounds thereof, and (3) at least one member of the group consisting of oxides of alkaline earth metals.

A related class of catalyst compositions further comprises at least one alkali metal or compound thereof.

Alkali metals are selected from the group consisting of lithium, sodium, potassium, rubidium and cesium. Lithium, sodium and potassium, and especially lithium and sodium, are preferred alkali metals.

Alkaline earth metals are selected from the group consisting of magnesium, calcium, strontium and barium. Presently preferred members of this group are magnesium and calcium. Compositions derived from magnesia have been found to be particularly effective catalytic materials.

Further classes of catalysts compositions within the scope of this invention are mixed oxides of sodium, magnesium, manganese and boron characterized by the presence of the crystalline compound $NaB_2Mg_4Mn_2O_x$ wherein x is the number of oxygen atoms required by the valence states of the other elements, said compound having a distinguishing x-ray diffraction pattern. In its most active form, the compound is believed to correspond to the formula $NaB_2Mg_4Mn_2O_{11}$. While this crystalline compound has been found to be associated with highly effective oxidant compositions, it has further been found that still better results are obtained when the oxidant is characterized by both: (1) the presence of crystalline compound $NaB_2Mg_4Mn_2O_x$ and (2) a stoichiometric excess of of Mn relative to at least one of the other elements of the crystalline compound. In currently preferred oxidants of this type, a stoichiometric excess of Mn relative to B is provided. In a still more specific preferred embodiment excess amounts of Na and Mg, as well as Mn, are present in the mixed oxide composition relative to the amounts required by the amount of boron present to satisfy the stoichiometry of the compound $NaB_2Mg_4Mn_2O_x$.

The compositions of this invention are useful in a variety of hydrocarbon conversion processes. When the active form of the composition (i.e., the composition in an oxidized state) is contacted with methane at elevated temperatures (e.g., at temperatures within the range of about 500° to 1000° C.), methane is converted to higher hydrocarbon products. The compositions are also effective contact agents (i.e., catalysts) in oxidative dehydrogenation processes.

DETAILED DESCRIPTION OF THE INVENTION

While the composition of the present invention is referred to as a "catalyst", it will be understood that, under conditions of use, it serves as a selective oxidant, and, therefore, takes on the characteristics of a reactant during use. Thus, for example, the term "Mn-containing oxides" is meant to embrace both reducible oxides of Mn an reduced oxides of Mn, it being understood reducible oxides comprise the principal active component of the compositions.

Consider the requirements of the oxidant. For selective reaction to take place, the oxidant must release the proper quantity of oxygen in the reaction zone within the proper period of time. If this does not occur, either non-selective oxidation reactions result (forming $CO_x$), or the degree of conversion is restricted. Furthermore, the oxidant must be capable of being repeatedly regenerated. Minimal or no coke formation is desirable. The oxidant must exhibit long life; the oxidant must exhibit relatively constant performance over the time while sequentially: (1) achieving selective conversion of reactants and (2) being regenerated to its active state. Mechanisms for the acquisition and release of oxygen by the oxidant are not fully understood. Undoubtedly, both physical and chemical phenomena are involved. For example, the oxygen may be both physically adsorbed and chemically reacted to form compounds of higher oxidation states.

In the following formulae describing the compositions of this invention, the relative number of oxygens is designated by "x". This x is variable because the compositions may continually gain and lose oxygen during use. Thus setting a strict range of values for x would be imprecise and possibly misleading. Generally, the value ascribed to x falls within the range of the number of oxygens required in the higher oxidation states (the "active" or "oxidized" composition) to the number of oxygens required in the lower oxidation states (the "reduced" composition).

The catalysts of the present invention, in their active state, comprise at least one reducible oxide of at least one metal, which oxide when contacted with methane (or higher hydrocarbons) at synthesizing (or dehydrogenation) oonditions (e.g., at a temperature within the range of about 500° to 1000° C.) produces higher hydrocarbon products (or in the case of higher hydrocarbon dehydrogenation, dehydrogenated hydrocarbon products), coproduct water, and a reduced metal oxide. The term "reducible" is used to identify those oxides of metals which are reduced under the aforesaid conditions. The term "reducible oxides of metals" includes: (1) compounds described by the general formula $M_xO_y$ wherein M is a metal and x and y designate the relative atomic proportions of metal and oxygen in the composition and/or (2) one or more oxygen-containing metal compounds (i.e., compounds containing elements in addition to the metal and 0), provided that such oxides and compounds have the capability of producing higher hydrocarbon products from methane, or of producing dehydrogenated hydrocarbons from dehydrogenatable hydrocarbons, as described herein.

Effective agents for the conversion of methane to higher hydrocarbons have previously been found to comprise reducible oxides of metals selected from the group consisting of manganese, tin, indium, germanium, antimony, lead, bismuth and mixtures thereof. See U.S. Pat. Nos. 4,443,649; 4,444,984; 4,443,648; 4,443,645; 4,443,647; 4,443,644; and 4,443,646.

Reducible oxides of cerium, praseodymium, and terbium have also been found to be effective for the conversion of methane to higher hydrocarbons, particularly associated with an alkali metal component and/or an alkaline earth metal component. See U.S. Pat. Nos. 4,499,324 (Ce) and 4,499,323 (Pr) and also see commonly-assigned U.S. patent application Ser. No. 06/600,918 (Tb).

Reducible oxides of iron and ruthenium are also effective, particularly when associated with an alkali or alkaline earth component. See commonly-assigned U.S. patent application Ser. No. 06/600,730 (Fe) and U.S. Pat. Nos. 4,489,215 and 4,593,139 (Ru).

One class of preferred compositions is characterized by the substantial absence of catalytically effective Ni and the noble metals (e.g., Rh, Pd, Ag, Os, Ir, Pt and Au) and compounds thereof, to minimize the deleterious catalytic effects of such metals and compounds thereof. For example, at the conditions (e.g., temperatures) under which the present compositions are used, these metals tend to promote coke formation and oxides of these metals tend to promote formation of combustion products ($CO_x$) rather than the desired hydrocarbons. The term "catalytically effective" is used to identify that quantity of one or more of nickel and the noble metals and compounds thereof which, when present, substantially changes the distribution of products obtained when employing the compositions of this invention.

Other additives may be incorporated into the composition of this invention. For example, addition of a phosphorus component has been found to enhance the stability of the composition. When used, phosphorus may be present up to an amount providing an atomic ratio of P to the reducible metal oxide component (expressed as the metal e.g., Mn) of about 2/1. If phosphorus is employed, it is desirable to provide it during catalyst preparation in the form of phosphates of alkali metals (e.g., orthophosphates, metaphosphates and pyrophosphates). Pyrophosphates are preferred. Sodium pyrophosphate is particularly preferred. P can be provided in other forms though. Examples include orthophosphoric acid, ammonium phosphates and ammonium hydrogenphosphates.

Further examples of other components which may be present in the compositions of this invention are halogen and chalcogen components. Such components may be added either during preparation of the catalysts or during use. Methane conversion processes employing halogen-promoted, reducible metal oxides are disclosed in U.S. Pat. No. 4,544,784. Methane conversion processes employing chalcogen-promoted, reducible metal oxides are disclosed in U.S. Pat. No. 4,544,785.

CATALYST COMPOSITIONS

One broad class of compositions useful in the processes of this invention comprises:
(1) at least one reducible oxide of at least one metal which oxides when contacted with methane at synthesizing conditions are reduced and produce higher hydrocarbon products and water and
(2) at least one member selected from the group consisting of boron and compounds thereof.

The relative amounts of the two components used to form the catalyst is not narrowly critical. However, the preferred atomic ratio of the reducible metal oxide component (expressed as the metal, e.g., Mn) to the boron component (expressed as B) is within the range of about 0.1–20:1, more preferably within the range of about 0.5–5:1.

One narrower class of compositions useful in the processes of this invention comprises:
(1) at least one reducible metal oxide,
(2) at least one member of the group consisting of boron and compounds hereof, and
(3) at least one member of the group consisting of oxides of alkaline earth metals.

Preferred compositions contain more than about 10 wt. % of the alkaline earth component, more preferably they contain more than about 20 wt. % of the alkaline earth component. Reducible metal oxides are preferably present in an amount within the range of about 1 to 40 wt. % based on the combined weight of the metal (e.g., Mn) and the alkaline earth component, more preferably within the range of about 5 to 30 wt. %, and still more preferably within the range of about 5 to 20 wt. %.

Preferred catalysts of this class are mixed oxide compositions satisfying the following empirical formula:

$$MB_bC_cO_x$$

wherein M is the reducible metal component, B is boron, and C is the alkaline earth component and wherein b is within the range of about 0.1 to 10, c is within the range of about 0.1 to 100, and x is the number of oxygen atoms required by the valence states of the other elements. Preferably, b is within the range of about 0.1 to 4. Preferably, c is within the range of about 0.5 to 15, more preferably about 1 to 6.

A further class of compositions useful in the processes of this invention comprises:
(1) at least one reducible metal oxide,
(2) at least one alkali metal or compound thereof,
(3) at least one member of the group consisting of boron and compounds thereof, and
(4) at least one member of the group consisting of oxides of alkaline earth metals. Preferred catalysts of this class are mixed oxide compositions satisfying the following empirical formula:

$$MA_aB_bC_cO_x$$

wherein M is the reducible metal component, A is at least one alkali metal, B is boron, C is at least one alkaline earth metal and wherein a is within the range of about 0.01 to 10, b is within the range of about 0.1 to 20, c is within the range of about 0.1 to 100, and x is the number of oxygen atoms required by the valence states of the other elements. Preferably b is within the range of about 0.1 to 10. Preferably, c is within the range of about 1 to 7.

A particularly preferred class of catalysts useful in the processes of this invention are mixed oxide compositions containing Na, Mg, Mn and boron which compositions are characterized by the presence of the compound $NaB_2Mg_4Mn_2O_x$ wherein x is the number of oxygen atoms required by the valence states of the other elements present in the compound. This compound possesses a definite, distinguishing crystalline structure whose x-ray diffraction pattern is substantially as set forth in Table I. Minor shifts in interplanar spacing (d (A)) and minor variation in relative intensity (I/Io) can occur as will be apparent to one of ordinary skill in the art.

TABLE I

| X-Ray Diffraction Pattern of $NaB_2Mg_4Mn_2O_x$ | |
|---|---|
| d (A) | I/Io |
| 7.7 | 100 |
| 7.2 | 1 |
| 5.6 | 19 |
| 4.6 | 3 |
| 4.4 | 10 |
| 4.2 | 7 |
| 3.6 | 7 |
| 3.34 | 15 |
| 3.31 | 14 |
| 2.99 | 3 |
| 2.97 | 2 |
| 2.81 | 19 |
| 2.77 | 2 |
| 2.74 | 10 |
| 2.58 | 4 |
| 2.49 | 3 |
| 2.46 | 53 |
| 2.43 | 10 |
| 2.39 | 1 |

TABLE I-continued

X-Ray Diffraction Pattern of
NaB$_2$Mg$_4$Mn$_2$O$_x$

| d (A) | I/Io |
|---|---|
| 2.33 | 1 |
| 2.31 | 5 |

A still more particularly preferred class of catalysts useful in the processes of this invention are mixed oxide compositions containing Na, Mg and boron which compositions are characterized by: (1) the presence of the crystalline compound NaB$_2$Mg$_4$Mn$_2$O$_x$ and (2) a stoichiometric excess in the composition of Mn relative to at least one of the other elements of the crystalline compound. In this latter regard, a stoichiometric excess of Mn relative to boron is preferred. Still more preferred are excess amounts of Na, Mg and Mn relative to boron. Thus, this more particularly preferred class of catalysts contains additional redox active material (i.e., additional reducible oxides of Mn). For example, such redox active crystalline compounds as Mg$_6$MnO$_8$, MgMn$_2$O$_4$, Na$_{0.7}$MnO$_{2.05}$, NaMnO$_2$, Na$_3$MaO$_4$, etc., may be present in the mixed oxide composition.

CATALYST PREPARATION

The boron-promoted reducible metal oxide compositions may be supported by or diluted with conventional support materials such as silica, alumina, titania, zirconia and the like, and combinations thereof. When supports are employed, alkaline earth oxides, especially magnesia, are preferred.

The catalysts are conveniently prepared by any of the methods associated with similar compositions known in the art. Thus, such methods as precipitation, coprecipitation, impregnation, granulation, spray drying or dry-mixing can be used. Supported solids may be prepared by methods such as adsorption, impregnation, precipitation, co-precipitation, and dry-mixing. Thus, a compound of Mn,Sn,In,Ge,Pb,Sb,Bi,Pr,Tb,Ce,Fe and/or Ru and a compound of boron (and other components) can be combined in any suitable way. Substantially any compound of the recited components can be employed. Typically, compounds used would be oxides or organic or inorganic salts of the recited components.

To illustrate, when preparing a catalyst containing: (1) a reducible metal oxide componet (e.g., Mn), (2) an alkali metal component, (3) a boron component and (4) an alkaline earth component: one suitable method of preparation is to impregnate compounds of the fourth component of the composition with solutions of compounds of Mn, alkali metals, and/or boron. Suitable compounds for impregnation include the acetates, acetyl acetonates, oxides, carbides, carbonates, hydroxides, formates, oxalates, nitrates, phosphates, sulfates, sulfides, tartrates, fluorides, chlorides, bromides, or iodides. After impregnation the preparation is dried to remove solvent and the dried solid is calcined at a temperature selected within the range of about 300° to 1200° C. Particular calcination temperatures will vary depending on the compounds employed.

Preferably, the alkaline earth component is provided as the oxide. Preferably, the alkali metal component is provided as a basic composition of the alkali metal(s). Examples are sodium hydroxide, sodium acetate, lithium hydroxide, lithium acetate, etc. When P is employed as an additive, it has been found desirable to add the alkali metal and P to the composition as compounds such as the orthophosphates, metaphosphates, and pyrophosphates of alkali metals. Pyrophosphates are preferred. Sodium pyrophosphate is particularly preferred.

Preferably, the boron component is provided as boric acid, boric oxide (or anhydride), alkali metal borates, boranes, borohydrides, etc., especially boric acid or oxide.

Formation of the crystalline compound NaB$_2$Mg$_4$Mn$_2$O$_x$ may be accomplished by reacting active compounds of the substituent elements. Suitable compounds of the substituent elements have been described above and are illustrated below in the Examples. A suitable mixture of the reactive compounds is formed and heated for a time sufficient to form the crystalline material. Typically, a temperature of about 850° to about 950° C. is sufficient. When preparing mixed oxide compositions characterized by the presence of the crystalline compound, the composition is desirably incorporated with binders or matrix materials such as silica, alumina, titania, zirconia, magnesia and the like.

Regardless of which particular catalyst is prepared or how the components are combined, the resulting composite will generally be dried and calcined at elevated temperatures prior to use. Calcination can be done under air, H$_2$, carbon oxides, steam, and/or inert gases such as N$_2$ and the noble gases.

HYDROCARBON CONVERSION PROCESS

The catalyst compositions of the present invention are generally useful for hydrocarbon conversion processes. Contacting a hydrocarbon feed with the active composition produces hydrocarbon product, coproduct water, and a reduced catalyst composition. The reduced catalyst composition is readily reoxidized to an active state by contact with an oxidant such as air or other oxygen-containing gases. The process may be effected in a cyclic manner wherein the catalyst is contacted alternatively with a hydrocarbon feed and then with an oxygen-containing gas. The process may also be effected in a noncyclic manner wherein the catalyst is contacted concurrently with a hydrocarbon feed and an oxygen-containing gas. Operating conditions are not critical to the use of this invention, although temperatures are generally within the range of about 500° to 1000° C. Gas/solid contacting steps may be performed according to any of the known techniques: e.g., the solids may be maintained as fixed beds, fluidized beds, moving beds, ebullating beds, etc. Solids may be maintained in one contact zone or may recirculate between multiple contact zones (e.g., between oxygencontact and hydrocarbon-contact zones).

METHANE CONVERSION PROCESS

One more specific application for the compositions of this invention is the conversion of methane to higher hydrocarbon products. The process comprises contacting a gas comprising methane with a composition comprising a boron-promoted reducible metal oxide to produce higher hydrocarbon products, coproduct water, and a composition comprising a reduced metal oxide. In addition to methane, the feedstock may contain other hydrocarbon or nonhydrocarbon components, although the methane content should typically be within the range of about 40 to 100 volume percent, preferably about 80 to 100 volume percent, more preferably about 90 to 100 volume percent. Operating temperatures are generally within the range of about 500° to 1000° C. Although not narrowly critical in the context of this invention, both total pressure and methane partial pressures effect results. Preferred operating pressures are within the range of about 1 to 100 atmospheres, more preferably about 1 to 30 atmospheres.

As indicated in the description of hydrocarbon conversion processes, a variety of process embodiments, including various gas/solids-contacting modes, may be employed.

METHANE CONVERSION PROCESS (COFEED)

In one particular embodiment of the broader methane conversion processes of this invention, methane is contacted with a boron-promoted catalyst in the presence of a gaseous oxidant.

The gaseous oxidant is selected from the group consisting of molecular oxygen, oxides of nitrogen, and mixtures thereof. Preferably, the gaseous oxidant is an oxygen-containing gas. A preferred oxygen-containing gas is air. Suitable oxides of nitrogen include $N_2O$, $NO$, $N_2O_3$, $N_2O_5$ and $NO_2$. Nitrous oxide ($N_2O$) is a presently preferred oxide of nitrogen.

The ratio of hydrocarbon feedstock to gaseous oxidant gas is not narrowly critical. However, the ratio will desirably be controlled to avoid the formation of gaseous mixtures within the flammable region. The volume ratio of hydrocarbon/gaseous oxidant is preferably within the range of abut 0.1–100:1, more preferably within the range of about 1–50:1. Methane/gaseous oxidant feed mixtures containing about 50 to 90 volume % methane have been found to comprise a desirable feedstream.

Operating temperatures for this embodiment of the invention are generally within the range of about 300° 1200° C., more preferably within the range of about 500° to 1000° C. Best results for contact solids containing manganese have been found at operating temperatures within the range of about 800° to 900° C. If reducible oxides of metals such as In, Ge or Bi are present in the solid, the particular temperature selected may depend, in part, on the particular reducible metal oxide(s) employed. Thus, reducible oxides of certain metals may require operating temperatures below the upper part of the recited range to minimize sublimation or volatilization of the metals (or compounds thereof) during methane contact. Examples are: (1) reducible oxides of indium, (operating temperatures will preferably not exceed about 850° C.); (2) reducible oxides of germanium (operating temperatures will preferably not exceed about 850° C.); and (3) reducible oxides of bismuth (operating temperatures will preferably not exceed about 850° C.).

Operating pressures for the methane contacting step are not critical. However, both general system pressure and partial pressures of methane and oxygen have been found to effect overall results. Preferred operating pressures are within the range of about 0.1 to 30 atmospheres.

The space velocity of the gaseous reaction streams are similarly not critical, but have been found to effect overall results. Preferred total gas hourly space velocities are within the range of about 10 to 100,000 hr.$^{-1}$ more preferably within the range of about 600 to 40,000 hr. $^{-1}$.

Contacting methane and a reducible metal oxide to form higher hydrocarbons from methane also produces coproduct water and reduces the metal oxide. The exact nature of the reduced metal oxides are unknown, and so are referred to as "reduced metal oxides". Regeneration of reducible metal oxides in this "cofeed" embodiment of the present invention occurs "in situ"—by contact of the reduced metal oxide with the gaseous oxidant cofed with methane to the contact zone.

The contact solids may be maintained in the contact zone as fixed, moving, or fluidized beds of solids. A fixed bed of solids is currently preferred for this embodiment of the invention.

The effluent from the contact zone contains higher hydrocarbon products (e.g., ethylene, ethane and other light hydrocarbons), carbon oxides, water, unreacted hydrocarbon (e.g., methane) and oxygen, and other gases present in the oxygen-containing gas fed to the contact zone. Higher hydrocarbons may be recovered from the effluent and, if desired, subjected to further processing using techniques known to those skilled in the art. Unreacted methane may be recovered and recycled to the contact zone.

OXIDATIVE DEHYDROGENATION PROCESS

Another more specific application for the compositions of this invention is the dehydrogenation of dehydrogenatable hydrocarbons. The process comprises contacting a gas comprising a dehydrogenatable hydrocarbon with a composition comprising a boron-promoted reducible metal oxide to produce dehydrogenated hydrocarbon product, coproduct water, and a composition comprising a reduced metal oxide. Dehydrogenatable hydrocarbons include a wide variety of hydrocarbons: e.g., $C_{2+}$ alkanes, cycloalkanes, olefins, alkylaromatics, etc. The dehydrogenated product depends in part on the feedstock selected. For example, alkanes may be dehydrogenated to form olefins, diolefins, alkynes, etc., and olefins may be dehydrogenated to form diolefins, alkynes, etc. One preferred class of feedstock comprises $C_2$–$C_5$ alkanes (both branched and unbranched). One preferred process embodiment comprises oxidative dehydrogenation of $C_2$–$C_5$ alkanes to form the corresponding mono-olefins.

Operating temperatures are generally within the range of about 500° to 1000° C. Operating pressures are not narrowly critical. In general, the process is conducted within the parameters of the oxidative dehydrogenation art, but uses a novel catalyst.

EXAMPLES

The invention is further illustrated by reference to the following examples. Experimental results reported below include conversions and selectivities calculated on carbon mole basis. Space velocities are reported as gas hourly space velocities (hour$^{-1}$) and are identified below as "GHSV". Methane and methane/air contact runs were made after the solids had been heated to reaction temperature in a stream of heated nitrogen.

At the end of each methane contact run, the reactor was flushed with nitrogen and the solids were regenerated under a flow of air (usually at 800° C. for 30 minutes). The reactor was then again flushed with nitrogen and the cycle repeated. Results reported below are based on samples collected after the catalysts had "equilibrated", i.e., after any aberrant characteristics of freshly prepared catalyst had dissipated.

EXAMPLE 1

A catalyst was prepared by mixing boric acid and manganese (II) acetate in the following mole ratio, 2:3. The mixture was calcined in air at 800° C. for 16 hours. When the catalyst was contacted with methane at 800°

C. and 600 GHSV, the methane conversion was 25% with 27% selectivity to $C_2+$ hydrocarbon products.

Comparative Example A

When bulk manganese oxide ($Mn_2O_3$) was contacted with methane at 800° C. and 860 GHSV, the methane conversion was 30% with 4% selectivity to $C_2+$ hydrocarbon products.

EXAMPLE 2

A catalyst was prepared by mixing (in a ball mill) manganese dioxide (33.2 grams), boric acid (11.3 grams) and magnesia (42.3 grams) with sufficient water to make a paste. The paste was dried for 4 hours at 100° C. and then calcined in air at 900° C. for 16 hours. Table II shows one-minute cumulative results obtained when the catalyst was contacted with methane.

TABLE II

| Temp. (°C.) | GHSV | % Conversion | % Selectivity | | |
|---|---|---|---|---|---|
| | | | $C_2+$ | $CO_x$ | Coke |
| 825 | 1200 | 30.4 | 78.6 | 21.1 | 0.3 |
| 825 | 600 | 38.1 | 66.0 | 33.8 | 0.2 |
| 800 | 600 | 29.8 | 76.1 | 23.7 | 0.2 |

When the catalyst was contacted with an equal volume mixture of methane/air at 850° C. and a total GHSV of 2400 hr.$^{-1}$, the methane conversion obtained was 25% with 72% selectivity to $C_2+$ hydrocarbon product.

EXAMPLE 3

A catalyst was prepared by mixing (in a ball mill) manganese dioxide (33 grams), boric acid (11 grams), sodium hydroxide (15 grams) and magnesia (42 grams). This corresponds to an atomic ratio of Na/Mg/Mn/B of about 7/12/4/2. The mixture was calcined in air at 900° C. for 16 hours. The finished catalyst contained the crystalline compound $NaB_2Mg_4Mn_2O$, but also contained an amount of Na, Mg, and Mn in excess of the stoichiometric amount. Table III shows two-minute cumulative results obtained when the catalyst was contacted with methane.

TABLE III

| Temp. (°C.) | GHSV | % Conversion | % Selectivity | | |
|---|---|---|---|---|---|
| | | | $C_2+$ | $CO_x$ | Coke |
| 825 | 1200 | 34.5 | 62.2 | 37.7 | 0.1 |
| 850 | 2400 | 32.0 | 60.5 | 39.5 | 0.1 |
| 825 | 600 | 75.3 | 24.8 | 73.2 | 2.0 |
| 800 | 600 | 17.0 | 77.1 | 22.6 | 0.3 |

When the catalyst was contacted with an equal volume mixture of methane/air at 850° C. and a total GHSV of 2400 hr.$^{-1}$, the methane conversion was 24% with 70% selectivity to $C_2+$ hydrocarbon products.

EXAMPLE 4

A catalyst was prepared by dry mixing $Na_2B_4O_7$ $10H_2O$ (29.8 grams), $Mn(C_2H_3O_2)_2$ $4H_2O$ (76.5 grams) and magnesia (25 grams). This corresponds to an atomic ratio of Na/Mg/Mn/B of about 1/4/2/2. The mixture was calcined in air at 940° C. for 16 hours. The finished catalyst contained the crystalline compound $NaB_2Mg_6Mn_2O_x$ and did not contain a stoichiometric excess of any of the substituent elements. Table IV shows two-minute cumulative results obtained when the catalyst was contacted with methane.

TABLE IV

| Temp. (°C.) | GHSV | % Conversion | % Selectivity | | |
|---|---|---|---|---|---|
| | | | $C_2+$ | $CO_x$ | Coke |
| 825 | 1200 | 13.0 | 77.7 | 21.5 | 0.8 |
| 850 | 600 | 38.1 | 66.0 | 33.8 | 0.2 |
| 800 | 600 | 29.8 | 76.1 | 23.7 | 0.2 |

When the catalyst was contacted with an equal volume mixture of methane/air at 850° C. and at total GHSV of 2400 hr.$^{-1}$, the methane conversion was 28.5% with 69% selectivity to $C_2+$ hydrocarbon products.

EXAMPLE 5

A catalyst was prepared by ball milling manganese dioxide (32.2 grams), boric acid (11.3 grams), magnesia (42.3 grams) and lithium hydroxide (9.2 grams). The milled mixture was calcined in air at 900° C. for 16 hours. Table V shows cumulative results obtained when the catalyst was contacted with methane at 840° C.

TABLE V

| Run Length (seconds) | GHSV | % Conversion | % Selectivity | | |
|---|---|---|---|---|---|
| | | | $C_2+$ | $CO_x$ | Coke |
| 15 | 1200 | 36.7 | 77.5 | 17.1 | 5.4 |
| 15 | 2400 | 21.0 | 92.4 | 6.6 | 1.3 |
| 30 | 2400 | 16.2 | 93.1 | 5.6 | 1.2 |
| 60 | 1200 | 25.0 | 88.2 | 9.5 | 2.3 |

EXAMPLE 6 and Comparative Example B

A catalyts (Example 6) was prepared by mixing sodium acetate, boric acid, magnesia and ferrous nitrate in the following mole ratio, 1:2:4:2. The mixture was calcined in air at 940° C. for 16 hours. When the catalyst was contacted with an equal volume mixture of methane/air at 850° C. and a total GHSV of 2400 hr.$^{-1}$, the methane conversion was 22.5% with 67% selectivity to $C_2+$ hydrocarbon products.

A catalyst (Comparative Example B) was prepared as described above in Example 4 except the boron component was omitted. When the catalyst was contacted with an equal volume mixture of methane/air at 850° C. and a total GHSV of 2400 hr.$^{-1}$, the methane conversion was 18.2% with 41.0% selectivity to $C_2+$ hydrocarbon products.

EXAMPLE 7

A catalyst was prepared by ball milling boric acid (6.7 grams), $NaMnO_4$ $3H_2O$ (32.7 grams) and magnesia (40.0 grams). This corresponds to an atomic ratio of Na/Mg/Mn/B of about 3/18/3/2. The mixture was calcined in air at 850° C. for 16 hours. The finished catalyst contained the crystalline compound $NaMg_4Mn_2B_2O_x$ (as exhibited by the x-ray diffraction pattern shown in Table VI), but also contained an amount of Na, Mg and Mn in excess of the stoichiometric amount.

TABLE VI

| d (Å) | I/Io | d (Å) | I/Io |
|---|---|---|---|
| 7.76 | 100 | 2.18 | 3 |
| 7.18 | 4 | 2.12 | 37 |
| 5.67 | 20 | 2.11 | 12 |
| 4.87 | 9 | 2.09 | 4 |
| 4.61 | 4 | 2.05 | 31 |
| 4.38 | 15 | 2.00 | 9 |
| 4.25 | 9 | 1.95 | 18 |
| 3.59 | 14 | 1.87 | 10 |
| 3.46 | 2 | 1.82 | 3 |

TABLE VI-continued

| d (Å) | I/Io | d (Å) | I/Io |
|---|---|---|---|
| 3.34 | 30 | 1.79 | 3 |
| 3.31 | 18 | 1.76 | 2 |
| 3.00 | 5 | 1.70 | 3 |
| 2.97 | 4 | 1.62 | 5 |
| 2.82 | 22 | 1.59 | 8 |
| 2.74 | 16 | 1.55 | 2 |
| 2.67 | 6 | 1.54 | 15 |
| 2.58 | 9 | 1.51 | 10 |
| 2.53 | 4 | 1.49 | 13 |
| 2.50 | 7 | 1.41 | 7 |
| 2.45 | 63 | 1.39 | 5 |
| 2.43 | 19 | 1.38 | 4 |
| 2.39 | 2 | 1.37 | 3 |
| 2.33 | 2 | 1.36 | 3 |
| 2.31 | 10 | 1.26 | 6 |
| 2.29 | 15 | | |
| 2.23 | 4 | | |
| 2.21 | 2 | | |
| 2.19 | 2 | | |

A study of catalyst life was performed according to the cycle, methane contact/$N_2$ purge/air regeneration/$N_2$ purge. Methane contact was performed at 1200 GHSV for about one minute. Approximately 5 runs per hour were performed over a period exceeding 7 months. Table VII summarizes results obtained.

TABLE VII

| Cycle # | Temp. (°C.) | % Methane Conversion | % $C_2+$ Selectivity |
|---|---|---|---|
| 1350 | 815 | 18 | 82 |
| 4050 | 815 | 26 | 78 |
| 6750 | 815 | 23 | 78 |
| 9450 | 815 | 26 | 74 |
| 12,150 | 815 | 24 | 74 |
| 14,850 | 815 | 20 | 78 |
| 17,550 | 820 | 26 | 76 |
| 20,250 | 820 | 24 | 76 |
| 22,950 | 820 | 23 | 82 |
| 27,000 | 820 | 26 | 73 |

What is claimed:

1. In an improved method for converting methane to higher hydrocarbon products which comprises contacting a gas comprising methane at synthesizing conditions with a solid comprising at least one reducible oxide of at least one metal which oxides when contacted with methane at synthesizing conditions are, reduced and produce higher hydrocarbon products and water, the improvement which comprises conducting the contacting in the presence of a promoting amount of at least one member of the group consisting of boron and compounds thereof.

2. The method of claim 1 which the atomic ratio of the reducible metal oxide component (expressed as the metal) to the boron component (expressed as B) is within the range of about 0.1:1 to about 20:1.

3. The method of claim 1 wherein the atomic ratio of the reducible metal oxide component (expressed as the metal) to the boron component (expressed as B) is within the range of about 0.5:1 to about 5:1.

4. The method of claim 1 wherein the solid comprises reducible metal oxides selected from the group consisting of reducible oxides of Mn, Sn, In, Ge, Pb, Sb, Bi, Pr, Tb, Ce, Fe, Ru and mixtures thereof.

5. The method of claim 1 wherein the solid comprises reducible oxides of Mn.

6. The method of claim 1 wherein the reducible oxide and the boron promoter are associated with a support material.

7. The method of claim 1 wherein methane is converted to higher hydrocarbon products in a cyclic manner comprising contacting the solid alternately with a gas comprising methane and with a gaseous oxidant.

8. The method of claim 7 wherein the solid is contacted with a gas comprising methane at temperatures selected within the range of about 500° to about 1000° C.

9. The method of claim 1 wherein methane is converted to higher hydrocarbon products by contacting the solid concurrently with a gas comprising methane and a gaseous oxidant.

10. The method of claim 9 wherein said concurrent contact is conducted at temperatures selected within range of about 300° to about 1200° C.

11. The method of claim 9 wherein said concurrent contact is conducted at temperatures selected within the range of about 500° to about 1000° C.

12. The method of claim 9 wherein said concurrent contact is conducted at a temperature selected within the range of about 800° to about 900° C.

13. In an improved method for converting methane to higher hydrocarbon products which comprises contacting a gas comprising methane at synthesizing conditions with a solid comprising: (a) at least one reducible oxide of at least one metal which oxides when contacted with methane at synthesizing conditions are reduced and produce higher hydrocarbon products and water and (b) at least one member of the group consisting of alkaline earth metals and compounds thereof; the improvement which comprises conducting the contacting in the presence of a promoting amount of at least one member of the group consisting of boron and compounds thereof.

14. The method of claim 13 wherein the solid is a mixed oxide composition satisfying the empirical formula:

$$MB_bC_cO_x$$

wherein M is selected from the group consisting of Mn, Sn, In, Ge, Pb, Sb, Bi, Pr, Tb, Ce, Fe, Ru and mixtures thereof; B is boron; and C is at least one alkaline earth metal; and wherein b is within the range of about 0.1 to about 10, c is within the range of about 0.1 to about 100, and x is the number of oxygen atoms required by the valence states of the other elements.

15. The method of claim 14 wherein b is within the range of about 0.1 to about 4.

16. The method of claim 14 wherein c is within the range of about 0.5 to about 15.

17. The method of claim 14 wherein c is within the range of about 1 to about 6.

18. The method of claim 13 wherein the solid comprises reducible oxides of Mn.

19. The method of claim 14 wherein the mixed oxide composition comprises reducible oxides of Mn.

20. The method of claim 19 wherein M is Mn.

21. The method of claim 13 wherein element (b) is at least one member of the group consisting of oxides of alkaline earth metals.

22. The method of claim 21 wherein element (b) is magnesia.

23. The method of claim 21 wherein element (b) is calcia.

24. The method of claim 14 wherein C is Mg.

25. The method of claim 14 wherein C is Ca.

26. The method of claim 13 wherein the solid further comprises at least one member of the group consisting of alkali metals and compounds thereof.

27. The method of claim 26 wherein the alkali metal is sodium.

28. The method of claim 26 wherein the alkali metal is lithium.

29. The method of claim 26 wherein the solid is a mixed oxide composition satisfying the empirical formula:

$$MA_aM_bC_cO_x$$

wherein M is selected from the group consisting of Mn, Sn, In, Ge, Pb, Sb, Bi, Pr, Tb, Ce, Fe, Ru and mixtures thereof; A is at least one alkali metal; B is boron; C is at least one alkaline earth metal; and wherein a is within the range of about 0.01 to about 10, b is within the range of about 0.1 to about 20, c is within the range of about 0.1 to about 100, and x is the number of oxygen atoms required by the valence states of the other elements.

30. The method of claim 29 wherein b is within the range of about 0.1 to about 10.

31. The method of claim 29 wherein c is within the range of about 1 to about 7.

32. The method of claim 29 wherein the mixed oxide composition comprises reducible oxides of Mn.

33. The method of claim 32 wherein M is Mn.

34. The method of claim 29 wherein A is sodium.

35. The method of claim 29 wherein A is lithium.

36. The method of claim 29 wherein C is Mg.

37. The method of claim 29 wherein C is Ca.

38. The method of claim 29 wherein the solid contains Mn, Na, B and Mg and the mixed oxide composition is characterized by the presence of the crystalline compound $NaB_2Mg_4Mn_2O_x$.

39. The method of claim 38 wherein the mixed oxide composition is further characterized by an amount of Mn in the composition which is in excess of the stoichiometric amount relative to at least one of the other elements of said crystalline compound.

40. The method of claim 39 wherein a stoichiometric excess of Mn relative to boron is provided.

41. The method of claim 40 wherein the mixed oxide composition contains excess amounts of Na, Mg and Mn relative to the amounts required by the amount of boron present to satisfy the stoichiometry of said crystalline compound.

* * * * *